US00PP28330P2

(12) United States Plant Patent
Kordes

(10) Patent No.: US PP28,330 P2
(45) Date of Patent: Aug. 29, 2017

(54) FLORIBUNDA ROSE PLANT NAMED 'KORBENTGOL'

(50) Latin Name: *Rosa hybrida*
Varietal Denomination: KORbentgol

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 14/999,283

(22) Filed: Apr. 19, 2016

(51) Int. Cl.
*A01H 5/02* (2006.01)

(52) U.S. Cl.
USPC ..... Plt./146

(58) Field of Classification Search
USPC ..... Plt./146, 147
CPC ..... A01H 5/0222
See application file for complete search history.

*Primary Examiner* — Kent L Bell

(57) ABSTRACT

'KORbentgol' is a new and distinct variety of *Rosa hybrida* which is characterized by the combination of a compact and bushy growth habit, moderate plant vigor, excellent resistance to common rose diseases, and panicles of very-double orange flowers. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORbentgol'.

STATEMENT REGARDING PRIOR DISCLOSURES BY THE INVENTOR UNDER 37 C.F.R. 1.77(B)(6)

The first public disclosure of the claimed plant was made by the breeder in a press release on Jul. 18, 2015. 'KORbentgol' was not publically available or sold prior to one year before the date of the instant application.

BACKGROUND OF THE INVENTION

Parentage: The *Rosa hybrida* variety 'KORbentgol' is the result of a controlled cross-pollination breeding program carried out by the inventor in Klein Offenseth-Sparrieshoop, Germany. The objective of the said breeding program was to create a new and distinct rose plant with unique qualities, such as:

1. Uniform growth and flowering; and
2. Abundant, recurrent orange flowers; and
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORbentgol' from all other varieties known to the inventor.

'KORbentgol' is a seedling selection which resulted from the controlled pollination of an unnamed *Rosa hybrida* seedling developed and owned by the same inventor, the seed parent, and *Rosa hybrida* 'KORassenet' (unpatented), the pollen parent, during the summer of 2001. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2002 from the seedling beds due to its superior characteristics and asexually propagated for further evaluation. This new and distinctive rose variety was given the name 'KORbentgol'.

Asexual Reproduction: 'KORbentgol' was first asexually propagated by bud grafting in July of 2002 at the inventor's nursery in Klein Offenseth-Sparrieshoop, Germany. Subsequently, 'KORbentgol' has been successfully propagated by stem cuttings and bud grafting in Jackson County, Oreg. These initial and other subsequent propagations conducted in controlled environments demonstrate that 'KORbentgol' reproduces true to type in successive generations of asexual reproduction.

SUMMARY OF THE INVENTION

The following characteristics have been repeatedly observed and represent the distinguishing characteristics of the new *Rosa hybrida* cultivar 'KORbentgol'. These traits, in combination, distinguish 'KORbentgol' as a new and distinct cultivar.

1. *Rosa hybrida* 'KORbentgol' exhibits a compact, bushy growth habit; and
2. *Rosa hybrida* 'KORbentgol' exhibits excellent resistance to rust, black spot disease, *Botrytis* and powdery mildew; and
3. *Rosa hybrida* 'KORbentgol' exhibits panicles of 3 to 4 orange flowers held upright; and 4. *Rosa hybrida* 'KORbentgol' exhibits very-double flowers of medium size for a floribunda rose; and
5. *Rosa hybrida* 'KORbentgol' exhibits flowers with a moderate plant vigor.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORbentgol', taken from a two year old plant.

DETAILED BOTANICAL DESCRIPTION

The following is a detailed botanical description of a new and distinct variety of *Rosa hybrida* known as 'KORbentgol', based upon observations made in October of 2015 from two year old, field-grown plants in Jackson County, Oreg. Those skilled in the art will appreciate that certain characteristics will vary with older or, conversely, with younger plants. 'KORbentgol' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORbentgol' and comparisons with the parents and closest known comparator variety of *Rosa hybrida* are provided below.

General plant description:

*Growth rate*.—Moderately vigorous.

*Growth habit*.—Compact and bushy.

*Mature dimensions*.—100 cm tall and 60 cm wide, on average.

*Cold hardiness*.—Grown successfully in USDA Hardiness Zones 6.

*Propagation*.—Stem cuttings and bud grafting.

*Disease resistance*.—Excellent resistance to powdery mildew (*Sphaerotheca pannosa*), blackspot (*Diplocarpon rosae*), rust (*Phragmidium* sp.) and *Botrytis* diseases under normal growing conditions in Jackson County, Oreg.

Root system: Moderately branched, fibrous root system with roots evenly distributed throughout the soil profile, from shallow to deep.

Stems:

*Stem color*.—Young stems are Yellow-Green Group 146C; mature stems are Yellow-Green Group 146B.

*Anthocyanin intonations*.—Intonations of Greyed-Purple Group 183B are present on young stems.

*Stem surface texture*.—Young stems are smooth while mature stems exhibit a rough texture.

*Stem dimensions*.—Typical mature stems are approximately 500 mm long and 5 mm in diameter.

*Prickles*.—Incidence — Typically 4 prickles per 10 cm of stem, on average. Size — Average length is 4 mm long. Immature prickle color — Greyed-Orange Group 174A. Mature prickle color — Greyed-Orange Group 175A, and senescing to Greyed-Brown Group N199B. Shape — Deeply concave. Texture — Smooth.

Leaves:

*Arrangement*.—Imparipinnate compound leaves; mature axillary leaves consisting of 7 leaflets.

*Attachment*.—Petiolate.

*Dimensions*.—165 mm long and 100 mm wide.

*Abundance*.—Very abundant; approximately 100 leaves.

*Stipules*.—Size — 15 mm long and 4 mm wide. Stipule color — Yellow-Green Group 146B. Anthocyanin intonations — Very slight intonations of Greyed-Purple Group 183D are present on the adaxial surface of the midrib. Stipitate glands — A limited number of stipitate glands are present on the margins, and very few stipitate glands are found on the abaxial surface. Margins — With stipitate glands. Texture, adaxial surfaces — Glabrous. Texture, abaxial surfaces — Leathery. Apex — Apiculate. Base — Fused to the petiole.

*Petiole*.—Length — Average 12 mm. Diameter — Average 2.0 mm. Petiole color, adaxial surface — Yellow-Green Group 146A. Petiole color, abaxial surface — Yellow-Green Group 146B. Anthocyanin intonations — In juvenile foliage, heavy intonations of Greyed-Purple Group 183A are present on the petiole. Margins — Evenly spaced stipitate glands. Prickles — None present. Stipitate glands — A limited number of stipitate glands are present on the margins of the adaxial surface. Texture — Glabrous. Strength — Strong.

*Rachis*.—Length — Ranges from 12 to 15 mm. Diameter — Average 1.5 to 2.0 mm. Color — Yellow-Green Group 146B. Anthocyanin intonations — In juvenile foliage, heavy intonations of Greyed-Purple Group 183A are present on the rachises. Margins — Entire, with occasional stipitate glands present. Prickles — None present. Stipitate glands — A limited number of stipitate glands are present on the margins only. Texture and pubescence — Smooth and glabrous.

*Leaflets*.—Dimensions — Average size of the terminal leaflet is 55 mm long and 35 mm wide. Shape — Elliptic. Apex — Acute. Base — Obtuse. Margins — Serrated; slightly undulated. Luster, texture and pubescence; adaxial surface — Semi-glossy, smooth and glabrous. Luster, texture and pubescence; abaxial surface — Matte, smooth and glabrous. Juvenile foliage color, adaxial surface — Yellow-Green Group 146B. Juvenile foliage color, abaxial surface — Yellow-Green Group 146C. Mature foliage color, adaxial surface — Yellow-Green Group 147A. Mature foliage color, abaxial surface — Yellow-Green Group 147C. Anthocyanin intonations — In juvenile foliage, heavy intonations of Greyed-Purple Group 183A are present throughout the adaxial and abaxial surfaces of the terminal leaflet. These intonations are also present along the margins and the marginal zone of the adaxial surfaces of the other juvenile leaflets, as well as most of the abaxial surface of the other juvenile leaflets. Venation — Reticulate. Petiolule — — 2 mm long and 1 mm in diameter. Petiolule color, adaxial surface — Yellow-Green Group 146D. Petiolule color, abaxial surface — Yellow-Green Group 145C. Anthocyanin intonations — In juvenile foliage, heavy intonations of Greyed-Purple Group 183A are present on the petiolules. Prickles — None present. Texture, adaxial and abaxial surfaces — Smooth. Margins — Entire, with occasional stipitate glands present.

Inflorescence:

*Inflorescence type.*—Panicles with 3 to 4 flower buds. Flowers are held upright.

*Blooming habit.*—Recurrent; floriferous.

*Size.*—70 mm tall and 30 mm wide, on average.

*Peduncle.*—Length — 3.5 to 4.5 cm average length. Diameter — 2.5 to 3.5 mm average diameter. Color — Yellow-Green Group 146B. Anthocyanin intonations — Strong intonations of Greyed-Purple Group 183B are present on approximately 50 percent of the peduncle. Strength — Strong to somewhat strong. Texture and pubescence — Glabrous.

Flowering laterals: Present below the initiation of inflorescence. Generally 1 to 2 flowering laterals are present, with 1 flower per flowering shoot.

Bud:

*Bud form.*—Short; pointed ovoid.

*Size.*—Upon opening, 25 mm in length from base of receptacle to distal end of bud and 20 mm diameter at its widest point.

*Texture.*—Smooth.

*Color, as sepals first unfold.*—Yellow-Orange Group 16B, with upper portions and margins having intonations of Red Group 44C.

*Color when one-quarter open, inner side.*—Marginal zone — Orange Group 29B, with intonations of Red Group 43C. Middle zone — Orange Group 29B. Basal zone — Yellow Group 13A.

*Color when one-quarter open, outer side.*—Marginal zone — Orange Group 24B, with intonations of Red Group 43C. Middle zone — Yellow-Orange Group 14C, with intonations of Orange Group 24B. Basal zone — Yellow-Orange Group 14C.

Flower:

*Pedicel.*—Length — 3.0 to 4.5 cm average length. Diameter — 1.5 to 3.0 mm average diameter. Color — Yellow-Green Group 146B. Anthocyanin intonations — Strong intonations of Greyed-Purple Group 183B are present on approximately 90 percent of the pedicel. Strength — Somewhat strong. Texture and pubescence — Rugose, with stipitate glands.

*Calyx.*—General — Comprised of five polysepalous sepals, with very weak foliaceous appendages present on one to two of the five sepals.

*Diameter of calyx.*—30 to 35 mm, at anthesis.

*Sepals.*—Color, upper surface — Yellow-Green Group 146B. Color, lower surface — Yellow-Green Group 146A. Anthocyanin intonations — Intonations of Greyed-Purple Group 183B present on the lower surface. Size — 22 mm long and 8 mm wide, on average. Apex — Apiculate. Base — Flat at union with receptacle. Quantity — Five. Upper surface — Pubescent with fine hairs. Lower surface — Stipitate glands present. Margins — Pubescent with a limited number of stipitate glands.

*Corolla.*—General shape of corolla — Shallow cup; open.

*Shape of corolla when viewed from the side.*—Upon opening, upper portion — Flat. Upon opening, lower portion — Flattened convex. Open flower, upper portion — Flat. Open flower, lower portion — Concave. Dimensions — Medium size for a floribunda rose. When open, the average flower diameter is 70 mm and the average flower height is 45 mm. Fragrance — Moderate fruity and sweet fragrance. Duration — On the plant for 3 to 6 days. Senesced petals drop away cleanly. Petals — Petal count — Exhibits very double flowers with an average of 45 petals under normal conditions. Petal reflex — Petals are somewhat reflexed. Timing of petal reflex — Simultaneous. Petal margin — Entire. Petal shape — Obovate. Apex — Obtuse. Base — Cuneate. Dimensions — 20 to 30 mm long and 20 to 35 mm wide. Texture, inner surface — Smooth. Texture, outer surface — Smooth. Petal color, upon opening — Outermost petals, inner surface — Marginal zone — Red Group 37A to 37B. Middle zone — Orange Group 29C. Basal zone — Yellow Group 2C. Outermost petals, outer surface — Marginal zone — Orange Group 29B. Middle zone — Orange Group 29B. Basal zone — Yellow Group 2A. Innermost petals, inner surface — Marginal zone — Orange-Red Group 30D. Middle zone — Orange Group 28C. Basal zone — Yellow Group 9A. Innermost petals, outer surface — Marginal zone — Orange Group 29A. Middle zone — Orange Group 29B. Basal zone — Yellow Group 13C. Basal petal spots, upon opening — None observed. Petal color, after opening — Outermost petals, inner surface — Marginal zone — Orange-Red Group 33D. Middle zone — Orange Group 28D. Basal zone — Yellow Group 6B. Outermost petals, outer surface — Marginal zone — Orange-Red Group 32D. Middle zone — Orange-Red Group 32D. Basal zone — Yellow Group 3B. Innermost petals, inner surface — Marginal zone — Orange-Red Group 33D. Middle zone — Orange Group 29C. Basal zone — Yellow Group 3A. Innermost petals, outer surface — Marginal zone — Orange-Red Group 33D. Middle zone — Orange Group 29C. Basal zone — Yellow Group 5C. Basal petal spots, after opening — None observed. General Tonality — On open flower, Orange Group 29B. No change in general tonality at the end of the second day; thereafter the general tonality is Red Group 37D; after the fourth day the general tonality is Red Group 49C.

*Petaloids.*—Quantity — 7 petaloids per flower, on average. Dimensions — Approximately 10 to 15 mm long and 4 to 6 mm wide. Color, inner surface — Marginal zone — Orange-Red Group 32C. Middle zone — Orange Group 29B. Basal zone — Yellow Group 3A to 3B. Color, outer surface — Marginal zone — Orange Group 29B. Middle zone — Orange Group 29B. Basal zone — Yellow Group 2B. Margins — Very irregular; Entire to undulated to indented. Shape — Deltoid to obovate. Apex — Obtuse. Base — Attenuate. Texture, inner and outer surfaces — Smooth.

Reproductive organs:

*Stamens.*—Quantity — Approximately 60, on average, and regularly arranged around the styles. Anthers — Shape — Reniform. Dimensions — 2 mm long and 1 mm wide, on average. Color — Yellow-Orange Group 17C. Pollen — Present; moderate. Color is Yellow-Orange Group 17A. Filaments — Color — Yellow-Orange Group 14B. Length — 9 mm.

*Pistils*.—Quantity — Average; approximately 30. Stigmas — Size — 1 mm. Location — Slightly inferior in position to anthers. Color — Greyed-Orange Group 163C. Styles — Length — Approximately 7 mm long. Color — Yellow-Green 145A, with intonations of Red Group 45D on the upper 25 percent.

*Ovary*.—Dimensions — 8 mm long and 5 mm in diameter. Color — Green-White Group 157C.

*Receptacle*.—Shape — Funnel-shaped. Dimensions — Approximately 12 mm high and 7 mm wide. Surface texture and pubescence — Smooth and slightly pubescent. Color — Yellow-Green Group 147B, with intonations of Greyed-Purple Group 187B. Texture — Glabrous.

Hips and seed formation: Not observed.

COMPARISONS WITH THE PARENTS

The new rose plant may be distinguished from its seed parent, a *Rosa hybrida* breeding line developed by the inventor, by the following combination of characteristics:

1. 'KORbentgol' exhibits orange flowers, whereas the seed parent exhibits yellow flowers.
2. 'KORbentgol' exhibits a very double petal count, whereas the seed parent exhibits a semi-double petal count.
3. 'KORbentgol' exhibits a medium size flower for a floribunda rose, whereas the seed parent exhibits a small flower.

The new rose plant may be distinguished from its pollen parent, *Rosa hybrida* 'KORassenet', by the following combination of characteristics:

1. 'KORbentgol' exhibits orange flowers, whereas 'KORassenet' exhibits yellow flowers.
2. 'KORbentgol' exhibits a medium size flower for a floribunda rose, whereas 'KORassenet' exhibits a large flower.
3. 'KORbentgol' exhibits moderate plant vigor, whereas 'KORassenet' exhibits strong plant vigor.

COMPARISON WITH THE MOST SIMILAR *ROSA* CULTIVAR KNOWN TO THE INVENTOR

For a comparison, several physical characteristics of the *Rosa hybrida* variety 'KORfocgri', a rose variety from the same inventor which is described and illustrated in U.S. Plant Pat. No. 22,353, are compared to 'KORbentgol' in Chart 1.

CHART 1

| Characteristic | 'KORbentgol' | 'KORfocgri' |
|---|---|---|
| General tonality of the flower, at anthesis. | Orange Group 29B. | Orange-Red Group 30A. |
| Color of outside petals, upon opening. | (inner surface) Marginal zone Red Group 37A to 37B, Middle zone Orange Group 29C, and Basal zone Yellow Group 2C. | Red Group 49A. |
| Abundance of foliage. | Very abundant. | Average abundance. |

That which is claimed:

1. A new and distinct variety of rose plant named 'KORbentgol', as described and illustrated herein.

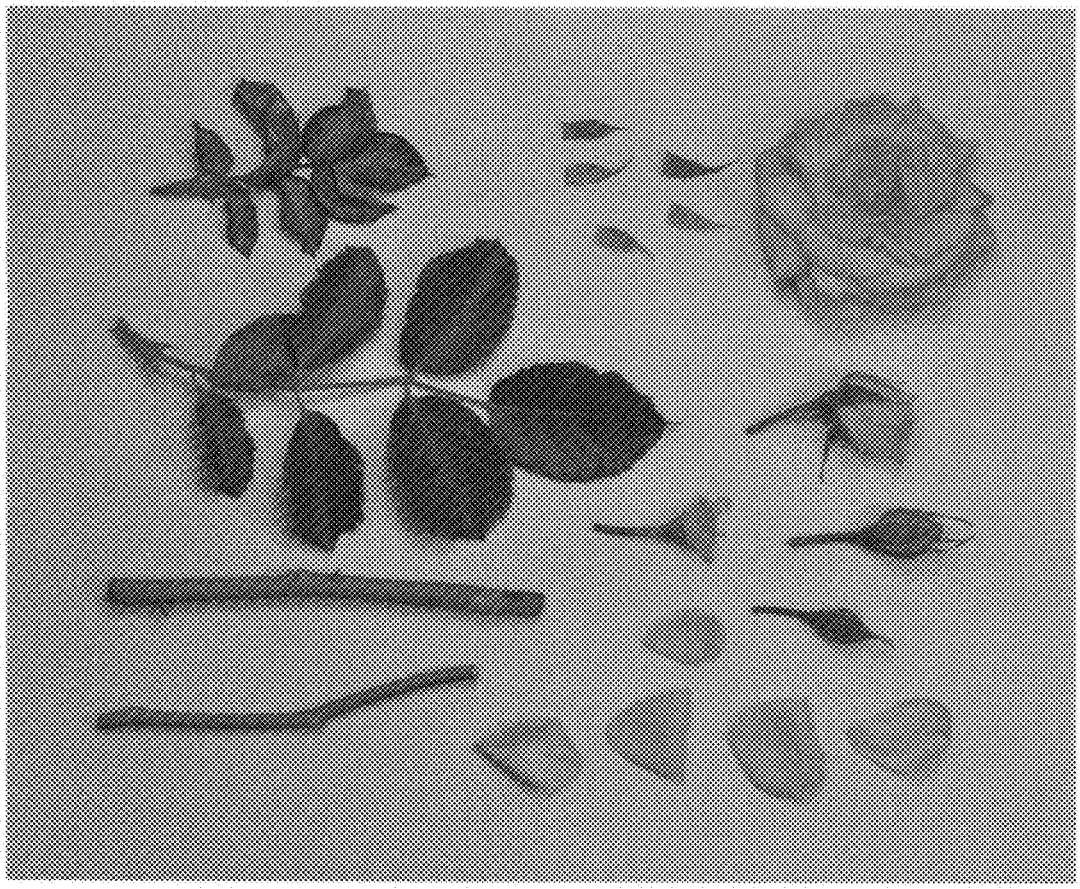

* * * * *